| United States Patent [19] | [11] | 4,174,345 |
|---|---|---|
| Kaiser | [45] | Nov. 13, 1979 |

[54] SYNTHESIS OF STEROIDS

[76] Inventor: Emil T. Kaiser, 5634 S. Woodlawn Ave., Chicago, Ill. 60637

[21] Appl. No.: 929,932

[22] Filed: Aug. 1, 1978

[51] Int. Cl.$^2$ .............................................. C07J 9/00
[52] U.S. Cl. ............................... 260/397.1; 260/397.2
[58] Field of Search ........................... 260/397.2, 397.1

[56] References Cited
PUBLICATIONS

Corey et al., "Tetrahedron Letters," (1976), p. 809.

*Primary Examiner*—Elbert L. Roberts

[57] ABSTRACT

In the synthesis of sterols wherein methoxyethoxymethyl groups in an ether linkage are attached to the nucleus of the sterol to protect the sterol nucleus during other steps of the synthesis and the sterols are thereafter treated to remove the methoxyethoxymethyl groups and set free the hydroxyl groups, the improvement in which the sterols being treated with zinc bromide are held in a methylene chloride solution containing a small amount of an aliphatic alcohol having from 1 to 6 carbon atoms.

12 Claims, No Drawings

SYNTHESIS OF STEROIDS

This invention relates to the synthesis of steroids and more particularly to such procedures in which a methoxyethoxymethyl group in an ether linkage is cleaved from a steroid nucleus.

BACKGROUND

In my copending patent application Ser. No. 816,478 filed July 18, 1977 I describe the synthesis of 25-hydroxycholesterol from hyodeoxycholic acid. In this synthesis the steroid nucleus is protected from interaction with reagents subsequently utilized for the extension of the hyodeoxycholic acid side chain by one carbon atom.

Hyodeoxycholic acid has two hydroxyl groups in its steroid nucleus, a 3α- and a 6α-hydroxyl. At an early stage in this synthesis, the 6α-hydroxyl is eliminated and a 5,6-double bond introduced. The α-hydroxyl is epimerized to a 3β-hydroxyl, and as disclosed in said application this 3β-hydroxyl group is protected with a group that is resistant to the alkaline reducing agents which are involved in the side chain elongation procedure. Methoxyethoxymethyl (MEM) is such a group, and in said application I describe the formation of an MEM-ether which is the 3β-(methoxyethoxymethoxy)-5-cholenic acid methyl ester. As disclosed, this MEM-ether may be formed by mixing 3β-hydroxy-5-cholenic acid ester with MEM halide in the presence of diisopropyl ethylamine.

With the steroid nucleus so protected, the 3β-(methoxyethoxymethoxy)-5-cholenic acid ester may be subjected to a series of steps in which it is treated with a reducing agent to reduce the 24-carboxylic ester groups to a 24-hydroxyl group suitably using as a reducing agent a complex of aluminum hydride with sodium, potassium or lithium, to obtain 3β-(β-methoxyethoxymethoxy)-24-hydroxy-4-cholene, and this may be mixed with p-toluenesulfonyl halide in pyridine solution and allowed to react to replace the hydroxyl at position 24 with OTs, and the resulting compound in turn may be reacted with a metallic cyanide such as sodium cyanide to replace the OTs group at position 24 with CN thus completing the extension of the carbon chain.

Then, as disclosed in my application Ser. No. 816,478, the steroid having the extended side chain may be treated with solid zinc bromide in methylene chloride solution to remove the MEM group and restore OH at the position 3 of the steroid nucleus.

One such treatment using zinc bromide for deprotection of certain MEM ethers is described by E. J. Corey, S. L. Graf and T. Ulrich in *Tetrahedron Letters*, 809 (1976). The resulting compound is 3β-hydroxy-25-cyano-5-cholene.

In a further series of steps the cyano group of the 3β-hydroxy-25-cyano-5-cholene is transformed into a carboxyl group by refluxing in ethanol solution with potassium hydroxide, and by acidification the free acid, 3β-hydroxy-5-homocholenic acid, is obtained. This, in turn, may be refluxed in methanol solution with p-toluenesulfonic acid as a catalyst to obtain 3β-hyroxy-5-homocholenic acid methyl ester. The resulting ester may be mixed with a methyl magnesium Grignard reagent in tetrahydrofuran and allowed to react to obtain 25-hydroxycholesterol which may be transformed to 25-hydroxy-7-dehydrocholesterol, and this, in turn, may be irradiated with ultraviolet light to obtain synthetic 25-hydroxycholecalciferol, a biologically active steroid, described by J. W. Blunt and H. F. DeLuca in *Biochemistry* 8, 671 (1969).

In repeated practice of the synthesis above outlined it was found that the yield of 3β-hydroxy-5-homocholenic acid varied in different runs, which meant that for some reason the full yield of the desired steroid was not being consistently obtained. Accordingly, I set about to discover the reason for the failure to obtain uniformly high yields and to discover methods for correcting this difficulty.

SUMMARY

I discovered that when an MEM group is used as a protectant for the hydroxyl groups of the sterol nucleus and the MEM group is later removed by treatment with zinc bromide in methylene chloride solution, this cleavage and removal is not in all instances complete, and I have further discovered that by the addition of a small amount of an aliphatic alcohol to the methylene chloride in which the sterol is treated, the yield of the resulting sterol from which the MEM group is removed, is consistently high.

DISCLOSURE OF THE INVENTION

My invention is applicable to any sterol the nucleus of which is protected by an MEM group and in any situation where it is desired to separate this group from the sterol nucleus. The sterol to be treated may be any methoxyethoxymethyl ether of a 3β-hydroxy sterol, particularly in the synthesis above described at the step in which the MEM group is cleaved from 3β-(2-methoxyethoxymethoxy)-25-cyano-5-cholene.

To carry out my improved process I may add the sterol to methylene chloride as a solvent therefor. To the solution, I add an aliphatic alcohol having from 1 to 6 carbons which may be methanol, ethanol, propanol, amyl alcohol or hexanol. Methanol or ethanol is preferred. The amount of the alcohol may vary from an appreciable or detectable amount up to about five volume percent based on the volume of methylene chloride. A very small amount (any amount more than 0 volume percent) based on the methylene chloride, can be expected to contribute some improvement but amounts of about 5 percent or more are detrimental to the cleavage function, and for reasons we will later explain, should not be used. A particular range for the amount of the alcohol is from 1 to 3 percent with about 2 percent being optimum, these percentages being by volume based on the methylene chloride.

Zinc bromide is added to the solution as in the prior practice, and the solution is agitated, suitably by a mechanical stirer, to bring the zinc bromide into suspension in the solution and to hold it in suspension until cleavage of the MEM group is completed.

To determine when cleavage is completed, the resulting sterol may be subjected to spectroscopic examination or may be subjected to thin layer chromatography, to ascertain the disappearance of the MEM sterol characteristics. Usually 4 or 5 hours treatment as described is sufficient, but treatment may be continued for up to 10 hours or more to make certain of full cleavage.

I believe the cleavage function requires or is due to the "Lewis Acid" effect of the zinc bromide on the sterol, but when the alcohol is used in an amount approaching about 5% of the solvent, the Lewis acid effect is diminished and that when used in an amount of about 5 volume percent or more, based on the methylene chloride, the Lewis acid effect becomes very substantially reduced.

Further, I find that in the absence of alcohol, this treatment with zinc bromide causes a precipitate to form and I believe this precipitate ties up the MEM sterol and the zinc bromide in a complex to prevent the cleavage reaction while these reactants are in precipitated form. It appears that in the presence of a sufficient amount of alcohol this precipitate does not form, or if at first it does form, a sufficient amount of alcohol will cause the precipitate to redissolve. It is my belief that the alcohol, when used in an adequate amount, in some way inhibits the formation of the precipitate and thus produces more effective cleavage of the MEM groups, but in stating this belief, I make no disclaimer if the effectiveness of the alcohol is found to be better explained on some other basis.

To determine the applicability of the improved procedure to MEM sterol ethers generally, I prepared the MEM ether of cholesterol as set forth in the following example 1.

EXAMPLE 1

Preparation of the Methoxyethoxymethyl (MEM) Ether of Cholesterol 3.87 g of cholesterol (1/100 mole) was dissolved in 40 ml of methylene chloride and 1.87 g of methoxyethoxy methyl chloride and 1.93 g of diisopropylethyl amine were added. After being stirred for 5 hours at room temperature, the reaction mixture was diluted with 40 ml of ether and washed with water. The organic layer was dried and evaporated. The viscous residue weighed 4.7 g (calculated yield 4.75 g) and its spectrum showed the absence of a free hydroxyl group. This cholesteryl-MEM ether preparation was used without purification for the zinc bromide cleavage described.

I then treated the MEM-cholesterol ether in methylene chloride with zinc bromide according to the method of Corey, Garf and Ulrich as set forth in *Tetrahedron Letters,* 809 (1976). This treatment is reported in the following Example 2.

EXAMPLE 2

Zinc Bromide Cleavage of MEM-Cholesteryl Ether 4.7 g of MEM-cholesteryl ether was dissolved in 40 ml of methylene chloride, and 2.25 g of zinc bromide was added. On stirring at room temperature strong discoloration was noticed, and a precipitate started to form. The mixture was stirred overnight, then the precipitate was removed by filtration. On washing with methylene chloride, the swollen lumps on the filter became nearly white. This off-white precipitate was dissolved in ether, the ether solution washed with water, dried, and evaporated. The residue was extracted with hot methanol in several portions. A dark colored residue remained, showing the presence of unchanged MEM-cholesteryl ether on measurement of the ir spectrum. This residue could not be separated in two components by chromatography or crystallization.

From the methanol extract, after cooling and several recrystallizations, cholesterol was obtained.

In a separate experiment I treated the same MEM-cholesteryl ether as was treated in Example 1, in methylene chloride solution containing an aliphatic alcohol, in accordance with the improved procedure as set forth herein, and this is reported in the following Example 3.

EXAMPLE 3

Zinc Bromide Cleavage of MEM-Cholesteryl Ether 12.7 g of cholesteryl-MEM ether was dissolved in 40 ml of methylene chloride, and 0.6 ml of methanol was added. Then, 2.25 g of zinc bromide was added, and the mixture was stirred. After a few minutes, discoloration occurred, and a precipitate started to form, but this soon disappeared. Stirring at room temperature was continued overnight, the clear solution freed from some remaining unreacted zinc bromide by filtration, and diluted with ether. After washing with water, the organic layer was dried and evaporated. The solid residue was crystallized from methanol, and the crystals indentified by melting point (144°–146° C.) and infrared spectra, as cholesterol. Neither in the cholesterol crystals nor in the small amount of residue remaining after the evaporation of the ethanol mother liquor could any uncleaved MEM-ether be found, as would be indicated by methanol insolubility or from the infrared absorption spectrum.

A comparison of the procedures and results obtained in Example 3 with the corresponding procedures and results of Example 2 demonstrates the benefit contributed by the alcohol in the methylene chloride solution.

In another experiment I utilized hexanol in place of methanol as the aliphatic alcohol, and this experiment is reported in the following Example 4.

EXAMPLE 4

Cleavage of MEM-Cholesterol Ether with Zinc Chloride in Methylene Chloride-Hexanol Solution The procedure of Example 3 was repeated with the exception that instead of 0.6 ml of methanol, 0.6 ml of hexanol was added. From 4.7 g MEM-cholesterol ether a nearly quantitative recovery of cholesterol was obtained, the same as in Example 3.

In one experiment I utilized 3$\beta$-(methoxyethoxymethoxy)-5-cholenic acid methyl ester and carried out the cleavage of MEM in accordance with the method illustrated by Example 14 of my patent application Ser. No. 816,478 in which the alcohol is not used in the sterol solvent. The procedures and results obtained are reported in the following Example 5.

EXAMPLE 5

Zinc Bromide Cleavage of 3$\beta$-(methoxyethoxymethoxy)-5-Cholenic Acid Methyl Ester The MEM-ether of the 3$\beta$-(methoxyethoxymethoxy)-5-cholenic methyl ester was prepared according to Example 13 of co-pending patent application Ser. No. 816,478, page 27. One gram of this MEM-ether (2.10 mmole) was dissolved in 10 ml of methylene chloride, 2.36 g of zinc bromide (10.5 mmole) was added, and the mixture stirred overnight at room temperature. After dilution with 50 ml of ether the reaction mixture was washed with an aqueous sodium bicarbonate solution, then with water, the organic layer dried over MgSO$_4$ and the solvent evaporated. The remaining oily residue (99% yield) could not be recrystallized, and from ir and nmr data was found to be a mixture of uncleaved MEM-ether and the free hydroxyl compound.

I conducted another experiment similar to that reported in Example 5 but including the use of the alcohol in the sterol solvent. The procedures and results of this experiment are reported in the following Example 6.

EXAMPLE 6

The above Example 5 was repeated with the use of methylene chloride containing 1½% of methanol as the reaction medium. During stirring at room temperature, the color of the solution turned deep purple. After 10 hours of stirring, ether was added, the solvent mixture washed with water, the organic layer dried, and the solvent evaporated. A yellow solid remained which was found to be identical with the 3β-hydroxy-5-cholenic acid methyl ester by thin layer chromatography, by nmr spectra, and by its infrared absorption spectrum, in which only the free hydroxyl compound's spectrum appeared. Atomic absorption trace analysis indicated that, if zinc was present at all, the amount was less than 5 ppm.

The effectiveness of the zinc bromide cleavage of 3β-methoxyethoxymethoxy steroids in methylene chloride solutions containing a small quantity of aliphatic alcohol is further confirmed by a comparison of Example 6 with Example 5.

EXAMPLE 7

Zinc Bromide Cleavage of 3β-(methoxyethoxymethoxy)-25-cyano-5-cholene

In Example 14 of my copending application Ser. No. 816,478, the 3β-MEM ether of the 25-cyano-5-cholene intermediate was converted to 3β-hydroxy-5-homocholenic acid. I found that variation in yields of the homocholenic acid resulted from incomplete cleavage of the 3β-(methoxyethoxymethoxy)-25-cyano-5-cholene with zinc bromide in methylene chloride solution. The cyano derivative was a product of the 3β-(methoxyethoxymethoxy)-24-p-toxyloxy-5-cholene-potassium cyanide reaction from which it was extracted in crude form. This crude cyano derivative-containing extract was dissolved in methylene chloride, stirred overnight with zinc bromide at room temperature and then, again without purification, saponified; 3β-hydroxy-5-homocholenic acid was obtained from the saponification mixture, with variations of yields between different runs. The ir and nmr absorption spectra of the crude product of the reaction between the 3β-(methoxyethoxymethoxy)-24-p-tosyloxy-5-cholene and potassium cyanide showed that the crude product was a mixture of 3β-(methoxyethoxymethoxy)and 3β-hydroxy-derivatives of 25-cyano-5-cholene. Crystallization attempts and chromatographic procedures failed to separate the two compounds, and also, repetition of the zinc bromide treatment in methylene chloride did not remove the remainder of the MEM group. When 1½% methanol was added to the methylene chloride solution, then the zinc bromide treatment resulted in the complete cleavage of the MEM-ether. For further clarification, the synthesis of the 3β-hydroxy-5-cholene through the MEM-ether route was repeated with the isolation and identification of each of the intermediates. Protection of the 3β-hydroxyl by the MEM group starts with the synthesis of 3β-(methoxyethoxymethoxy)-5-cholenic acid methyl ester, according to Example 13, patent application Ser. No. 816,478, page 27. The melting point of this compound, crystallized from pentane, was found to be 44°-45° C. Additional analytical data, not listed in the prior patent application, are the following: Anal. Calcd for $C_{29}H_{48}O_5$, C, 73.07; H, 10.15; O, 16.78. Found: C, 73.03; H, 10.28; O, 16.53. Ir (CHCl$_3$): 1730 cm$^{-1}$ (C=O); 1110 cm$^{-1}$ (C-O-C). Nmr (CHCl$_3$): δ3.4 (s, 3H, —PCH$_3$); δ0.67 (s, 3H, c-18-CH$_3$); δ1.00 (s, 3H, C-19-CH$_3$).

Reduction of the ester derivatives with Vitride (sodium bis[β-methoxyethoxy] aluminum hydride) yielded the 3β-(methoxyethoxymethoxy)-24-hydroxy-5-cholene. This compound, previously not isolated, was crystallized from hexane with mp 83°-84° C. Anal. Calcd for $C_{28}H_{48}O_4$, C, 74.95; H, 10.78; O, 14.26. Found: C, 75.72; H, 10.69; O, 14.28. Ir (CHCl$_3$); 3610 cm$^{-1}$, 3490 cm$^{-1}$ (OH); no C=O; 1110 cm$^{-1}$ (C-O-C). Nmr (CDCl$_3$); δ3.40 (s, 3H, —OCH$_3$); δ1.00 (s, 3H, C-19-CH$_3$); δ0.67 (s, 3H, C-18-CH$_3$).

The 24-hydroxy derivative was allowed to react with p-toluenesulfonyl chloride in pyridine solution. From the reaction mixture the previously not isolated 3β-(methoxyethoxymethoxy)-24-p-tosyloxy-5-cholene was crystallized from heptane with mp 93°-94° C. Anal. Calcd for $C_{35}H_{54}O_6S$: C, 69.73; H, 9.03; O, 15.92; S, 5.32. Found: C, 69.70; H, 9.24; O, 15.72; S, 5.12. Ir (CHCl$_3$): no OH; 2940 cm$^{-1}$, 2860 cm$^{-1}$, 1360 cm$^{-1}$, 1110 cm$^{-1}$. Nmr (CDCL$_3$): δ7.2-7.9 (Abq, 4H, aromatic); δ3.40 (s, 3H, —OCH$_3$); δ2.43 (s, 3H, Ar-CH$_3$); δ1.00 (s, 3H, C-19-CH$_3$); δ0.70 (s, 3H, C-18-CH$_3$).

The 24-p-tosyloxy derivative was allowed to react with potassium cyanide. From the reaction mixture, the previously not isolated 3β-(methoxyethoxymethoxy)-25-cyano-5-cholene was crystallized from heptane solution with a mp of 55°-56° C. Anal. Calcd for $C_{29}H_{47}O_3N$: C, 76.10; H, 10.35; O, 10.49; N, 3.06. Found: C, 76.21; H, 10.44; O, 10.76; N, 2.88. Ir (CHCl$_3$): 2250 cm$^{-1}$ (CN). Nmr (CDCl$_3$): δ3.40 (s, 3H, —OCH$_3$); δ1.02 (s, 3H, C-19-CH$_3$); δ0.67 (s, 3H, C-18-CH$_3$).

One gram of the crystallized 3β-(methoxyethoxymethoxy)-25-cyano-5-cholene was dissolved in a mixture of 20 ml of methylene chloride and 0.30 ml of methanol, and the solution was stirred with 2.5 g of zinc bromide overnight. The purple reaction mixture was diluted with ether, washed with water and the organic layer dried. Solvents were evaporated, the yellow oily residue dissolved by warming in heptane and decolorized with charcoal. From the filtered heptane solution, on chilling, 0.68 g of 3β-hydroxy-25-cyano-5-cholene crystallized out (yield 85%), with mp 183°-184° C. Anal. Calcd for $C_{25}H_{39}NO_3$: C, 81.24; H, 10.64; N, 3.79; O, 4.33. Found: C, 81.30; H, 10.74; N, 3.59; O, 4.51. Ir(CHCl$_3$): 3610 cm$^{-1}$, 3450 cm$^{-1}$ (OH); 2250 cm$^{-1}$ (CN). Nmr (CDCL$_3$): δ5.25-5.49 (m, 1H, vinyl); δ1.00 (s, 3H, C-19-CH$_3$); δ0.68 (s, 3H, C-18-CH$_3$). The elemental analysis and the mp data, together with the previously not recorded ir and nmr data, confirm the indentity of the 3β-hydroxy-25-cyano-5-cholene, prepared through the MEM-ether route, with the 3β-hydroxy-25-cyano-5-cholene, prepared through the (2-tetrahydropyranyloxy)-route, of Example 8, patent application Ser. No. 816,478, page 22.

The effectiveness of the zinc bromide cleavage of 3β-methoxyethoxymethoxy-steroids in methylene chloride solutions containing less than 5% aliphatic alcohol was further sustained by this example.

While only certain embodiments and certain variations of my invention have been described, it will be apparent to those skilled in this art that other embodiments may be practiced and that many changes may be made all within the spirit of the invention, and all such embodiments and changes are considered to be embraced and included within the scope of the claims.

What is claimed is:

1. In a process wherein a methoxyethoxymethoxy ether of a 3β-hydroxy steroid is treated with zinc bromide to cleave methoxyethoxymethoxy groups therefrom, the step of bringing zinc bromide into contact with said sterol and a solution of methylene chloride and an aliphatic alcohol having one to six carbons, said alcohol being in any appreciable amount up to about 5% by volume of said methylene chloride until cleavage of said methoxyethoxymethoxy groups is completed.

2. A process as set forth in claim 1, in which said solution is agitated and said zinc bromide is contained in suspended form within said solution.

3. A process as set forth in claim 1, in which said alcohol is in an amount of from 1 to 3% by volume of said methylene chloride.

4. A process as set forth in claim 3, in which said alcohol is in an amount of about 2 volume percent based on said methylene chloride.

5. A process as set forth in claim 1, in which said alcohol is methanol.

6. A process as set forth in claim 1, in which said alcohol is ethanol.

7. A process as set forth in claim 1, in which said sterol is held in such solution for a period of from 5 to 10 hours.

8. In a process wherein a methoxyethoxymethoxy ether of a 3β-hydroxy steroid is treated with zinc bromide to cleave methoxyethoxy methoxy groups therefrom, the step of bringing zinc bromide into contact with said sterol in a solution of the methylene chloride and an alphatic alcohol having from 1 to 6 carbons, said alcohol being in an amount less than 5% by volume of said methylene chloride, but in an amount sufficient to prevent formation of a precipitate from the solution or to dissolve a precipitate if formed, until a cleavage of methoxyethoxymethoxy groups is completed.

9. A process as set forth in claim 8, in which said alcohol is from 1 to 3% by volume by of said methylene chloride and which includes the step of agitating said solution to bring said zinc bromide into suspension in said solution.

10. A process as set forth in claim 1, in which said sterol is the methoxyethoxymethoxy cholesteryl ether.

11. A process as set forth in claim 1, in which said sterol is 3β-(methoxyethoxymethoxy)-5-cholenic acid methyl ester.

12. A process as set forth in claim 1, in which said sterol is 3β-(methoxyethoxymethoxy)-25-cyano-5-cholene.

* * * * *